United States Patent [19]

Imai et al.

[11] Patent Number: 5,556,862

[45] Date of Patent: Sep. 17, 1996

[54] PHARMACEUTICAL COMPOSITIONS CONTAINING ISOQUINOLINE DERIVATIVES

[75] Inventors: Shoichi Imai, Miura-gun; Ken-ichi Mabuchi, Osaka; Minoru Kawamura, Katoh-gun, all of Japan

[73] Assignee: Nippon Zoki Pharmaceutical Co., Ltd., Osaka, Japan

[21] Appl. No.: 360,630

[22] Filed: Dec. 21, 1994

[30] Foreign Application Priority Data

Dec. 28, 1993 [JP] Japan ................................ 5-351481

[51] Int. Cl.⁶ .......................... A61K 31/47; A61K 31/52
[52] U.S. Cl. ...................... 514/307; 514/309; 514/265
[58] Field of Search .................... 514/307, 309, 514/265

[56] References Cited

U.S. PATENT DOCUMENTS

| | | | |
|---|---|---|---|
| 4,035,366 | 7/1977 | Szentmiklosi et al. | 260/253 |
| 4,814,336 | 3/1989 | Szentmiklosi et al. | 514/263 |
| 4,820,838 | 4/1989 | Freisz et al. | 544/268 |
| 4,956,371 | 9/1990 | Shoupe et al. | 514/307 |

FOREIGN PATENT DOCUMENTS

| | | |
|---|---|---|
| 50-46818 | 4/1975 | Japan . |
| 62-167781 | 7/1987 | Japan . |
| 62-187411 | 8/1987 | Japan . |

OTHER PUBLICATIONS

Piskarev et al, *Biological Abstracts*, vol. 68, No. 3, Abstract No. 18993, 1979.

Lugnier et al, *Chemical Abstracts*, vol. 117, No. 9, abstract No. 85778s, 1992.

Lugnier et al, *Pharmazie*, vol. 47, No.1, 1992, pp. 46–49.

*Primary Examiner*—Marianne M. Cintins
*Assistant Examiner*—William R. A Jarvis
*Attorney, Agent, or Firm*—Fisher, Christen & Sabol

[57] ABSTRACT

Pharmaceutical compositions containing an isoquinoline derivative exhibit an excellent inhibitory action to an isozyme of phosphodiesterase of the type IV (PDEIV). The active component of the pharmaceutical composition is an isoquinoline derivative which is represented by the general formula:

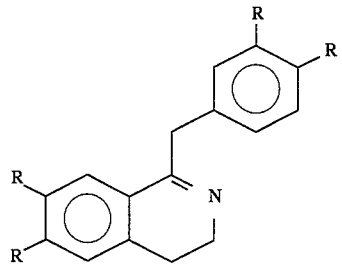

wherein R is an ethoxy group, or which is a pharmaceutically-acceptable salt of a compound represented by said formula. The isoquinoline derivatives have an excellent inhibitory action which is highly specific to PDEIV. They are highly useful as pharmaceuticals such as antidepressive agents, tranquilizers, antidemential agents, antiinflammatory agents, antiallergic agents, antiasthmatic agents, liver-protecting agents, and diuretic agents.

10 Claims, No Drawings

PHARMACEUTICAL COMPOSITIONS CONTAINING ISOQUINOLINE DERIVATIVES

FIELD OF THE INVENTION

The present invention relates to a pharmaceutical composition which contains at least one isoquinoline derivative and pharmaceutically-acceptable salts thereof as an effective component for inhibiting phosphodiesterase type IV.

BACKGROUND OF THE INVENTION

The intracellular information transmitters cAMP and cGMP play a role in regulating cell functions. Cyclic nucleotide phosphodiesterases are enzymes which decompose the substances cAMP and cGMP. The cyclic nucleotide phosphodiesterases are often abbreviated as "phosphodiesterases". They are classified into several isozymes. The molecular structure, the regulating functions, the distributions in tissues and in cells, and the specificity of each of those isozymes have been in a stage of clarification. At the same time, there have been brisk investigations for inhibitors which are specific to the isozymes of the phosphodiesterases and some inhibitors which are useful as pharmaceuticals, etc. have been found.

Phosphodiesterase type IV isozyme (hereinafter, referred to as PDEIV) is one of the isozymes of the phosphodiesterases. PDEIV is distributed in tissues and cells such as brain, kidney, spermary, inflammatory cells, etc. It has a low Km value to cAMP and is an enzyme which specifically decomposes cAMP. When the PDEIV is inhibited, the concentration of cAMP in tissues increases. Therefore, it has been known that inhibitors for PDEIV exhibit various pharmacological actions. For example, PDEIV inhibitors may exhibit action upon the central nervous system such as antidepressant, tranquillizing and antidemential actions. They may also possess antiinflammatory action due to inhibition of isolation of chemical mediators and also to inhibition of perfusion of neutrophils, a bronchodilating action, a relaxing action upon smooth muscles, a protective action upon livers, a diuretic action, etc.

Some isoquinoline derivatives have been known to exhibit pharmaceutical actions such as a peripheral dilating action and an antispasmodic action. For example, drotaverine and the like have been used as pharmaceuticals.

The present inventors have carried out an extensive study on the pharmacological actions of isoquinoline derivatives and found that the isoquinoline derivatives of the present invention have an excellent inhibiting activity with a high specificity to PDEIV.

SUMMARY OF THE INVENTION

The present invention provides pharmaceutical compositions which contain at least one isoquinoline derivative having an excellent PDEIV-inhibiting action as an effective component. The isoquinoline derivatives of the pharmaceutical compositions of the present invention are highly specific to PDEIV. The derivatives are represented by the following general formula and pharmaceutically acceptable salts thereof:

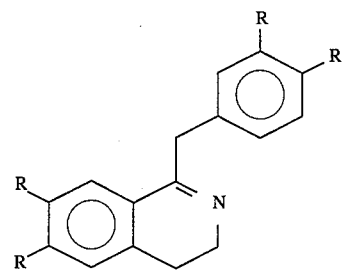

wherein R is hydrogen or an alkoxy group. The pharmaceutical compositions of the present invention include antidepressive agents, tranquilizers, antidemential agents, antiinflammatory agents, antiallergic agents, antiasthmatic agents, liver-protecting agents, and diuretic agents.

DETAILED DESCRIPTION OF THE INVENTION

The active component of the pharmaceutical composition of the present invention is at least one isoquinoline derivative which is represented by the general formula:

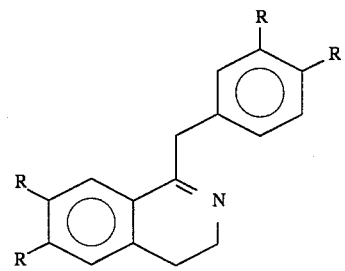

wherein R is hydrogen or an alkoxy group, and pharmaceutically acceptable salts thereof. The alkoxy group may be a linear or branched alkoxy group having one to ten carbon atoms such as methoxy, ethoxy, propoxy, isopropoxy, butoxy, isobutoxy, sec-butoxy, tert-butoxy, pentoxy, isopentoxy, neopentoxy, tert-pentoxy, hexoxy, dimethylbutoxy, heptoxy, octoxy, desoxy, etc.

The isoquinoline derivatives according to the present invention include the pharmaceutically-acceptable salts of the compounds represented by the above-given general formula. Exemplary of the pharmaceutically acceptable salts are acid addition salts with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluene-sulfonic acid, naphthalenesulfonic acid, sulfanic acid, theophylline-acetic acid, mixtures thereof, and the like. Preferred salts are the salts with hydrochloric acid or theophylline-acetic acid. The salts may be manufactured from the isoquinoline derivatives of the present invention in a free state or may be mutually converted from one to another by conventional means.

When the compounds of the present invention have stereoisomers such as cis-trans isomers, optical isomers, conformational isomers, etc. or exist in a form of hydrates, the present invention includes any of such stereoisomers and hydrates.

Examples of the compounds of the present invention which are particularly preferred are:

1-Benzyl-3,4-dihydroisoquinoline [Compound 1]
1-(3',4'-Dimethoxybenzyl)-6,7-dimethoxy-3,4-dihydroisoquinoline [Compound 2]
1-(3',4'-Diethoxybenzyl)-6,7-diethoxy-3,4-dihydroisoquinoline [Compound 3]
1-(3',4'-Diethoxybenzyl)-6,7-diethoxy-3,4-dihydroisoquinoline hydrochloride [Compound 4]
1-(3',4'-Diethoxybenzyl)-6,7-diethoxy-3,4-dihydroisoquinolinium-theophylline-7-acetate [Compound 5]
1-(3',4'-Diethoxybenzyl)-6,7-diethoxy-3,4-dihydroisoquinolinium-theophylline-7-acetate monohydrate [Compound 6]

The isoquinoline derivatives of the present invention may be prepared in conventional, known manner. The above-given compounds of the present invention have been disclosed, for example, in Japanese Laid-Open Patent Publications 50/046818, 62/167781, and 62/187411, and their corresponding U.S. Pat. Nos. 4,035,366, 4,820,838, and 4,814,336, respectively. The disclosures of said Japanese Patent Publications and said U.S. patents are herein incorporated by reference in their entireties.

U.S. Pat. No. 4,035,366 discloses the production of salts of dihydro- and tetrahydro-isoquinoline-theophylline-7-acetic acid by reaction of the isoquinoline with theophylline-7-acetic acid in the presence of a solvent which is preferably an alcohol such as methanol, ethanol, n-propanol, or isopropanol.

U.S. Pat. Nos. 4,814,336 and 4,820,838 disclose 1-(3',4'-diethoxybenzyl)-6,7-diethoxy-3,4-dihydroisoquinolinium-theophylline-7-acetate (Depogen). According to U.S. Pat. No. 4,820,838, Depogen is prepared by reacting equimolar amounts of 1-(3',4'-diethoxy-benzyl)-6,7-diethoxy-3,4-dihydro-isoquinoline with theophylline-7-acetic acid in an alcohol (preferably ethanol or isopropanol), cooling to precipitate a solid, and then filtering off the solid. In the process of U.S. Pat. No. 4,820,838 the crystalline monohydrate of 1-(3',4'-diethoxy-benzyl)-6,(7-diethoxy-3,4 -dihydro-isoquinolinium-theophylline-7-acetate and if desired of pure 1-(3',4'-diethoxybenzyl)- 6,7-diethoxy-3,4-dihydro-isoquinolinium-theophylline-7-acetate free of contaminating oxidation products is prepared by reacting 1-(3',4'-diethoxy-benzyl)-6,7-diethoxy-3,4 -dihydro-isoquinoline with theophylline-7-acetic acid in the presence of water and one or more organic solvents, and if desired dehydrating the 1-(3', 4'-diethoxy-benzyl)-6,7 -diethoxy-3,4-dihydro-isoquinolinium-theophylline-7-acetate-monohydrate thus obtained. The organic solvent may be dichloromethane, a ketone such as acetone, or an alcohol such as isopropanol.

Pharmacological actions of the isoquinoline derivatives of the present invention were demonstrated by preparing five types of isozymes of phosphodiesterase and then measuring the inhibitory activity of the isoquinoline derivatives and a control towards the isozymes:

1. Preparation of Phosphodiesterase Isozymes.

Each of the isozymes of the phosphodiesterases was prepared by conventional means. Thus, 10 g of freeze-dried powder of porcine artery was homogenized by adding 5 times as much (v/w) buffer (comprising 0.25M of sucrose, 10 mM of Tris hydrochloride (pH 7.8), 5 mM of magnesium chloride, 0.2 mM of ethylenebis(hydroxyethylenenitrilo)tetraacetic acid, 100 nM of p-toluenesulfonyl fluoride, 100 nM of leupeptine and 100 nM of pepstatin) thereto. This was centrifuged at 2,500 rpm for 20 minutes and the supernatant liquid was further centrifuged at 40,000 rpm for one hour. The resulting supernatant liquid was filtered and dialyzed to a solution (70 mM sodium acetate of pH 6.8 and 5 mM of 2-mercaptoethanol) containing the same protease inhibitor as in the above-given buffer.

The sample obtained by the dialysis was added to a DEAE-sepharose-FF column (Pharmacia) which was filled in a column equilibrated with the above-mentioned buffer and then eluted with the solution of sodium acetate with the linearly graded concentrations of 0.07–1.0M. Activity of each isozyme of phosphodiesterase in the eluted fractions was measured and the fractions where the activity was concentrated were collected for use as an enzyme source. In the present test system, isozymes of the types I, II, III, IV and V were eluted/fractionated in the fractions of 20 and 21; 30 and 31; 29; 61, and 67, respectively.

2. Method of Measuring the Phosphodiesterase Activity.

Reaction systems were prepared from 50 mM of Tris HCl (pH: 7.5), 6 mM of magnesium chloride, 1 mM of ethylenebis(hydroxyethylenenitrilo)tetraacetic acid, 2.5 mM of dithiothreitol, 2.5% of dimethyl sulfoxide, 0.025 mg/ml of 5'-nucleotide, 0.23 mg/ml of bovine serum albumin and 1–5 μg of each of the enzymes (the figures stand for the final concentrations). The reaction mixture solution was preincubated at 30° C. for 5–10 minutes. [$^3$H] cAMP or [$^3$H] cGMP was added thereto and the mixture was incubated at 30° C. for 10–15 minutes. A cationic exchange resin which was suspended in water was added to the reaction solution so that the unreacted [$^3$H] cAMP or [$^3$H] cGMP was adsorbed therewith to stop the reaction. Then the mixture was centrifuged at 2,000 g for five minutes. A part of the supernatant liquid was taken out and was subjected to measurement for its radioactivity by means of a liquid scintillation counter. The substance to be tested dissolved in dimethyl sulfoxide or in water, was added to the above reaction system and the inhibitory activity of said substance to each isozyme of phosphodiesterase was measured. The inhibitory activity ($IC_{50}$) of each substance is measured, for example, in μM of reacted [$^3$H] cAMP. So, the lower the amount of reacted [$^3$H] cAMP (or the lower the value of inhibiting activity) the more the isozyme was inhibited.

When the inhibitory activity of the substance to be tested towards the isozyme of type I was measured, [$^3$H] cAMP was used as a substrate in the presence of 5 μg/ml of calmodulin. In the case of the inhibitory activity measurement towards the type II isozyme, [$^3$H] cAMP was used as a substrate in the presence of 10 μM of cGMP. In the case of the type III isozyme, [$^3$H] cAMP was used as a substrate in the presence of 100 μM of Ro20-1724 {4,[3-butoxy-4-methoxyphenyl)-methyl]-2-imidazolidinone; an inhibitor which is specific to the type IV isozyme}. In the case of the type IV isozyme, [$^3$H] cAMP was used as a substrate in the presence of 10 μM of cilostazol (an inhibitor which is specific to the type III isozyme). In the case of the measurement of the type V isozyme, [$^3$H] cGMP was used as a substrate.

The inhibitory activity to each of the isozymes of phosphodiesterase was measured according to the above-mentioned test method and the result was that the compounds of the present invention exhibited a strong inhibitory action especially to the isozyme of the type IV. An example of the results is given in Table 1:

TABLE 1

Inhibitory Activity Results

| Substances Tested | Inhibitory Activity (IC$_{50}$) to PDEIV |
| --- | --- |
| Compound 4 of this Invention | 8.1 μM |
| Compound 6 of this Invention | 17.2 μM |
| Ro20-1724 (Control for Comparison) | 26.1 μM |

As exemplified by the results given in Table 1, the compounds of the present invention exhibit the same or even higher PDEIV-inhibiting activity as compared with Ro20-1724 which has been known as a very specific PDEIV inhibitor. Further, the PDEIV-inhibiting activity of the compounds of the present invention was so specific that said activity was 10 times or more stronger than that towards the other types of PDE isozymes.

As mentioned already, the concentration of cAMP in tissue increases when PDEIV is inhibited. Therefore, the pharmacological effects of PDEIV inhibitors includes actions on central nerves such as an antidepressive action, a tranquilizing action, antidemential action, etc., an antiinflammatory action due to the inhibition of isolation of chemical mediators and also due to the inhibition of perfusion of neutrophils, a bronchodilating action, a relaxing action for smooth muscles, a liver-protecting action, a diuretic action, etc.

Consequently, the substances of the present invention possess a very high utility as pharmaceuticals such as antidepressive agents, tranquilizing agents, antidemential agents, antiinflammatory agents, antiallergic agents, anti-asthmatic agents, liver-protecting agents, diuretic agents, etc. They may be used as medicaments for prevention and therapy of various diseases including central nervous system disease, such as depression and dementia, and other diseases or ailments such as inflammation, allergic diseases, asthma, liver diseases, kidney diseases, etc.

The isoquinoline derivatives of the present invention can be made into pharmaceutical preparations by combining one or more derivatives with one or more pharmaceutical carriers or diluents. They can be made into various types of preparations by conventional methods. Solid, semisolid, liquid or aerosol formulations which contain the derivatives for administration by oral or parenteral means are contemplated by the present invention.

In preparing the preparations, the substance of the present invention may be used either solely or jointly together with other pharmaceutically-active components.

In the case of the preparations for oral administration, the substance of the present invention alone or together with commonly-used excipients such as a suitable additive (e.g. lactose, sugar, glucose, mannitol, corn starch, potato starch, etc.) may be mixed with one or more binders such as crystalline cellulose, cellulose derivatives, gum arabicum, tragacanth solution, sodium alginate solution, gelatin, etc., one or more disintegrating agents such as corn starch, potato starch, potassium carboxymethylcellulose, etc., one or more lubricating agents such as talc, magnesium stearate, etc. and one or more other components including bulking agents, moisturizing agents, buffers, preservatives, perfumes and the like to obtain tablets, diluted powders, granules or capsules.

Alternatively, suppositories may be prepared by mixing the isoquinoline derivatives with fatty/oily bases (e.g. cacao butter), emulsified bases, water-soluble bases (e.g. Macrogol), hydrophilic bases, etc.

In the case of injections, it is possible to prepare the solutions or the suspensions of the isoquinoline derivatives in aqueous and nonaqueous solvents such as distilled water for injection, physiological saline solution, Ringer's solution, plant oil, synthetic fatty acid glycerides, higher fatty acid esters, propylene glycol, etc.

It is also possible, depending upon the state of the patient and the type of the disease, to prepare other pharmaceutical preparations containing the isoquinolilne derivatives which are suitable for the therapy. Exemplary of the other preparations are inhalating agents, aerosol agents, ointments, poultices, eye drops, etc.

The preferred doses of the isoquinoline derivative of the present invention may vary depending upon: (1) the subject receiving the administration (i.e. age, body weight, symptoms, etc. of the patient), (2) the form of the preparation, (3) the method for the administration, (4) the term for the administration, etc. To achieve a desired effect, 10–2,000 mg per day may be usually given to adults by the oral route in one dose per day or divided into several doses for administration several times a day.

In the case of a parenteral administration such as by injection, it is preferred that, due to the influence of adsorption, etc., a level of from ⅓ to ⅒ of the above-given oral dose is administered parenterally.

Some non-limiting examples of pharmaceutical formulations containing the substance of the present invention as an effective component are given in Tables 2 and 3:

TABLE 2

(Formulation Example 1; Tablet)

| Components | Amount per Tablet |
| --- | --- |
| Compound 6 of this Invention | 50 mg |
| Calcium citrate | 118 mg |
| Crystalline cellulose | 10 mg |
| Magnesium stearate | 2 mg |
| TOTAL | 180 mg |

TABLE 3

(Formulation Example 2; Injection)

| Components | Amount per Ampoule |
| --- | --- |
| Compound 4 of this Invention | 20 mg |
| Sodium chloride | q.s. |
| Distilled water for injection | q.s. |
| TOTAL | 1 ml |

What is claimed is:

1. A method for inhibiting phosphodiesterase type IV in a patient in need thereof comprising administering to said patient a therapeutically effective amount of an isoquinoline derivative of the general formula:

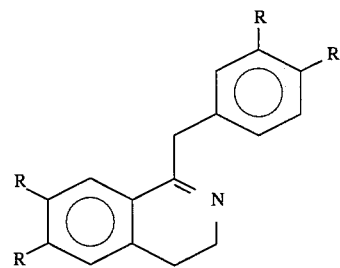

wherein R is an ethoxy group, or a pharmaceutically acceptable salt thereof.

2. A method as claimed in claim 1 wherein said salt is 1-(3',4'-diethoxybenzyl)-6,7-diethoxy-3,4-dihydro-isoquinoline hydrochloride.

3. A method as claimed in claim 1 wherein said salt is 1-(3',4'-diethoxybenzyl)-6,7-diethoxy-3,4-dihydro-isoquinolinium-theophylline- 7-acetate.

4. A method as claimed in claim 1 wherein said salt is 1-(3',4'-diethoxybenzyl)-6,7-diethoxy-3,4-dihydro-isoquinolinium-theophylline- 7-acetate monohydrate.

5. A method as claimed in claim 1 wherein at least one pharmaceutically acceptable salt of said isoquinoline derivative is administered to said patient.

6. A method for treating inflammation, central nervous system diseases, asthma, liver diseases, kidney diseases, or allergic diseases in a patient in need thereof comprising administering to said patient a therapeutically effective amount of an isoquiniline derivative to inhibit phosphodiesterase type IV, wherein said isoquinoline derivative is of the general formula:

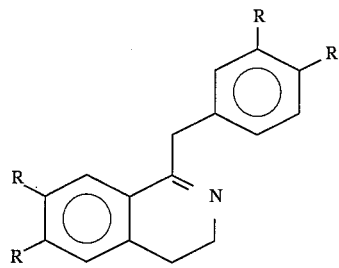

wherein R is an ethoxy group, or a pharmaceutically acceptable salt thereof.

7. A method as claimed in claim 6 wherein said salt is 1-(3',4'-diethoxybenzyl)-6,7-diethoxy-3,4-dihydro-isoquinoline hydrochloride.

8. A method as claimed in claim 6 wherein said salt is 1-(3',4'-diethoxybenzyl)-6,7-diethoxy-3,4-dihydro-isoquinolinium-theophylline- 7-acetate.

9. A method as claimed in claim 6 wherein said salt is 1-(3',4'-diethoxybenzyl)-6,7-diethoxy-3,4-dihydro-isoquinolinium-theophylline- 7-acetate monohydrate.

10. A method as claimed in claim 6 wherein at least one pharmaceutically acceptable salt of said isoquinoline derivative is administered to said patient.

* * * * *